(12) United States Patent
Tsuyama et al.

(10) Patent No.: US 10,131,656 B2
(45) Date of Patent: Nov. 20, 2018

(54) ORGANIC THIN FILM TRANSISTOR, METHOD OF MANUFACTURING ORGANIC THIN FILM TRANSISTOR, ORGANIC THIN FILM TRANSISTOR MATERIAL, ORGANIC THIN FILM TRANSISTOR COMPOSITION, ORGANIC SEMICONDUCTOR FILM, AND COMPOUND

(71) Applicants: FUJIFILM Corporation, Tokyo (JP); THE UNIVERSITY OF TOKYO, Tokyo (JP)

(72) Inventors: Hiroaki Tsuyama, Kanagawa (JP); Masashi Koyanagi, Kanagawa (JP); Eiji Fukuzaki, Kanagawa (JP); Masatoshi Yumoto, Kanagawa (JP); Yoshihisa Usami, Kanagawa (JP); Tetsuya Watanabe, Kanagawa (JP); Toshihiro Okamoto, Tokyo (JP); Junichi Takeya, Tokyo (JP)

(73) Assignees: FUJIFILM Corporation, Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/887,174

(22) Filed: Feb. 2, 2018

(65) Prior Publication Data
US 2018/0155338 A1   Jun. 7, 2018

Related U.S. Application Data

(63) Continuation of application No. PCT/JP2016/071310, filed on Jul. 20, 2016.

(30) Foreign Application Priority Data

Aug. 4, 2015 (JP) .................................. 2015-154181

(51) Int. Cl.
| | |
|---|---|
| *C07D 495/18* | (2006.01) |
| *H01L 51/00* | (2006.01) |
| *H01L 29/00* | (2006.01) |
| *C07D 471/02* | (2006.01) |
| *C07D 495/14* | (2006.01) |
| *H01L 29/786* | (2006.01) |
| *H01L 51/05* | (2006.01) |
| *H01L 29/45* | (2006.01) |
| *H01L 29/768* | (2006.01) |
| *C09B 57/08* | (2006.01) |

(52) U.S. Cl.
CPC ......... *C07D 471/02* (2013.01); *C07D 495/14* (2013.01); *C09B 57/08* (2013.01); *H01L 29/454* (2013.01); *H01L 29/768* (2013.01); *H01L 29/786* (2013.01); *H01L 51/0056* (2013.01); *H01L 51/05* (2013.01)

(58) Field of Classification Search
CPC . C07D 495/18; C07D 517/18; H01L 51/0545; H01L 29/00

USPC ............................................... 546/31; 257/40
See application file for complete search history.

(56) References Cited

U.S. PATENT DOCUMENTS

| | | | |
|---|---|---|---|
| 6,245,403 B1 | 6/2001 | Spahni et al. | |
| 6,491,749 B1 * | 12/2002 | Langhals | C07D 471/06 106/287.21 |

FOREIGN PATENT DOCUMENTS

| | | |
|---|---|---|
| JP | H03-042670 A | 2/1991 |
| JP | 2002-501497 A | 1/2002 |
| JP | 2002-527517 A | 8/2002 |
| JP | 2009-179794 A | 8/2009 |

(Continued)

OTHER PUBLICATIONS

International Search Report issued in PCT/JP2016/071310; dated Sep. 6, 2016.

(Continued)

*Primary Examiner* — Charanjit Aulakh
(74) *Attorney, Agent, or Firm* — Studebaker & Brackett PC

(57) ABSTRACT

An object of the present invention is to provide an organic thin film transistor that has an organic semiconductor film manufactured by using a compound having excellent solubility to an organic solvent and that has excellent carrier mobility, a novel compound, an organic thin film transistor material, an organic semiconductor film, an organic thin film transistor composition, and a method of manufacturing an organic thin film transistor using this. The organic thin film transistor according to the present invention has an organic semiconductor film containing a compound represented by Formula (1).

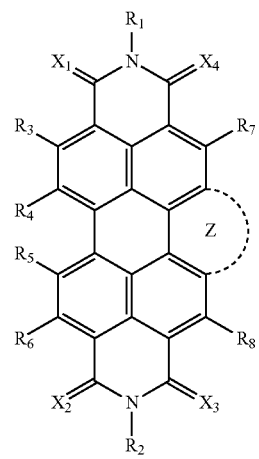

(1)

18 Claims, 2 Drawing Sheets

(56) References Cited

FOREIGN PATENT DOCUMENTS

| | | |
|---|---|---|
| JP | 2013-515785 A | 5/2013 |
| JP | 2013-207085 A | 10/2013 |
| WO | 2013/091279 A1 | 6/2013 |
| WO | 2014/175351 A1 | 10/2014 |

OTHER PUBLICATIONS

Written Opinion issued in PCT/JP2016/071310; dated Sep. 6, 2016.

Extended European Search Report issued by the European Patent Office dated Apr. 18, 2018, which corresponds to EP16832770.8-1116 and is related to U.S. Appl. No. 15/887,174.

Eccher, J. et al., "Thermal Evaporation versus Spin-Coating: Electrical Performance in Columnar Liquid Crystal OLEDs", ACS Applied Materials & Interfaces, vol. 7, No. 30, Jul. 13, 2015, pp. 16374-16381.

Zhan, X. et al., "Pyrene fused perylene diimides: synthesis, characterization and applications in organic field-effect transistors and optical limiting with high performance", Chemical Communications, vol. 51, No. 33, Mar. 16, 2015, pp. 7156-7159.

Xiao, C. et al., "Laterally Expanded Rylene Diimides with Uniform Branched Side Chains for Solution-Processed Air Stable n-Channel Thin Film Transistors", ACS Applied Materials & Interfaces, vol. 6, No. 20, Sep. 24, 2014, pp. 18098-18103.

Zhong, Y. et al., "Helical Ribbons for Molecular Electronics", Journal of the American Chemical Society, vol. 136, No. 22, May 20, 2014, pp. 8122-8130.

Hao, L. et al., "Perpendicularly entangled perylene diimides for high performance electron transport materials", Journal of Materials Chemistry C, vol. 1, No. 47, Oct. 17, 2013, pp. 7812-7818.

Zhang, Z. et al., "Electron-transporting PAHs with dual perylenediimides: syntheses and semiconductive characterizations", Chemical Communications, vol. 49, No. 28, Feb. 27, 2013, pp. 2882-2884.

\* cited by examiner

ORGANIC THIN FILM TRANSISTOR, METHOD OF MANUFACTURING ORGANIC THIN FILM TRANSISTOR, ORGANIC THIN FILM TRANSISTOR MATERIAL, ORGANIC THIN FILM TRANSISTOR COMPOSITION, ORGANIC SEMICONDUCTOR FILM, AND COMPOUND

CROSS-REFERENCE TO RELATED APPLICATIONS

This application is a Continuation of PCT International Application No. PCT/JP2016/071310 filed on Jul. 20, 2016, which claims priority under 35 U.S.C. § 119(a) to Japanese Patent Application No. 2015-154181 filed on Aug. 4, 2015. The above application is hereby expressly incorporated by reference, in its entirety, into the present application.

BACKGROUND OF THE INVENTION

1. Field of the Invention

The present invention relates to an organic thin film transistor, a method of manufacturing an organic thin film transistor, an organic thin film transistor material, an organic thin film transistor composition, an organic semiconductor film, and a compound.

2. Description of the Related Art

Since light weight, low cost, and flexibility can be obtained, an organic thin film transistor (organic TFT (thin film transistor)) having an organic semiconductor film (organic semiconductor layer) is used in a device using a logic circuit such as a field effect transistor (FET), a radio frequency identifier (RFID: RF tag), or a memory used in a liquid crystal display or an organic electro luminescence (EL) display.

As a compound for forming such an organic semiconductor film, JP2013-515785A discloses an organic semiconductive compound mainly having N-functionalized fused ring (aromatic) imide which is oxidized by thione.

SUMMARY OF THE INVENTION

Recently, in view of improving the performance of the organic thin film transistor, further improvement of the mobility of the organic thin film transistor is required.

In these circumstances, the present inventors have conducted research on a compound (organic semiconductor material, corresponding to the following comparative compound 2) disclosed in JP2013-515785A, the carrier mobility in a case where this compound was used in an organic semiconductor film of an organic thin film transistor did not satisfy the level necessarily required in these days.

The present inventors have conducted research on the cause thereof and have understood that low solubility of this compound to an organic solvent was related to carrier mobility.

Here, an object of the present invention is to provide an organic thin film transistor that has an organic semiconductor film manufactured by using a compound having excellent solubility to an organic solvent and that has excellent carrier mobility.

Another object of the present invention is to provide a novel compound and an organic thin film transistor material, an organic thin film transistor composition, and an organic semiconductor film which contain this compound.

Another object of the present invention is to provide a method of manufacturing an organic thin film transistor using the organic thin film transistor composition.

As a result of intensive studies on the above problems, the present inventors have found that a desired effect can be obtained by using a compound represented by Formula (1) described below, so as to conceive the present invention.

That is, the present inventors have found that the aforementioned objects can be achieved with the following configurations.

[1] An organic thin film transistor comprising: an organic semiconductor film containing a compound represented by Formula (1).

[2] The organic thin film transistor according to [1], in which, in Formula (1), the number of carbon atoms included in $R_1$ and the number of carbon atoms included in $R_2$ are each independently 30 or less.

[3] The organic thin film transistor according to [1] or [2], in which, in Formula (1), $R_1$ and $R_2$ each independently represent an alkyl group.

[4] The organic thin film transistor according to any one of [1] to [3], in which, in Formula (1), $R_1$ and $R_2$ are the same groups, $R_3$ and $R_6$ are the same groups, and $R_4$ and $R_5$ are the same groups.

[5] The organic thin film transistor according to any one of [1] to [4], in which, in Formula (1), Z is a 5-membered ring or a 6-membered ring.

[6] The organic thin film transistor according to any one of [1] to [5], in which the compound represented by Formula (1) is a compound represented by Formula (2).

[7] The organic thin film transistor according to any one of [1] to [6], in which, in Formula (1), at least two of $X_1$, $X_2$, $X_3$, and $X_4$ are formed of different atoms.

[8] A compound represented by Formula (1).

[9] The compound according to [8], in which, in Formula (1), the number of carbon atoms included in $R_1$ and the number of carbon atoms included in $R_2$ are each independently 30 or less.

[10] The compound according to [8] or [9], in which, in Formula (1), $R_1$ and $R_2$ each independently represent an alkyl group.

[11] The compound according to any one of [8] to [10], in which, in Formula (1), $R_1$ and $R_2$ are the same groups, $R_3$ and $R_6$ are the same groups, and $R_4$ and $R_5$ are the same groups.

[12] The compound according to any one of [8] to [11], in which, in Formula (1), Z is a 5-membered ring or a 6-membered ring.

[13] The compound according to any one of [8] to [12], in which the compound represented by Formula (1) is a compound represented by Formula (2).

[14] The compound according to any one of [8] to [13], in which, in Formula (1), at least two of $X_1$, $X_2$, $X_3$, and $X_4$ are formed of different atoms.

[15] An organic thin film transistor material containing the compound according to any one of [8] to [14].

[16] An organic thin film transistor composition containing the compound according to any one of [8] to [14].

[17] An organic semiconductor film containing the compound according to any one of [8] to [14].

[18] A method of manufacturing an organic thin film transistor, comprising: a step of coating a substrate with the organic thin film transistor composition according to [16] and drying the composition to form an organic semiconductor film.

As described below, according to the present invention, it is possible to provide an organic thin film transistor that has an organic semiconductor film manufactured by using a compound having excellent solubility to an organic solvent and that has excellent carrier mobility.

According to the present invention, it is possible to provide a novel compound and an organic thin film transistor material, an organic thin film transistor composition, and an organic semiconductor film which contain this compound.

According to the present invention, it is possible to provide a method of manufacturing an organic thin film transistor using the organic thin film transistor composition.

DESCRIPTION OF THE PREFERRED EMBODIMENTS

Figure 1:
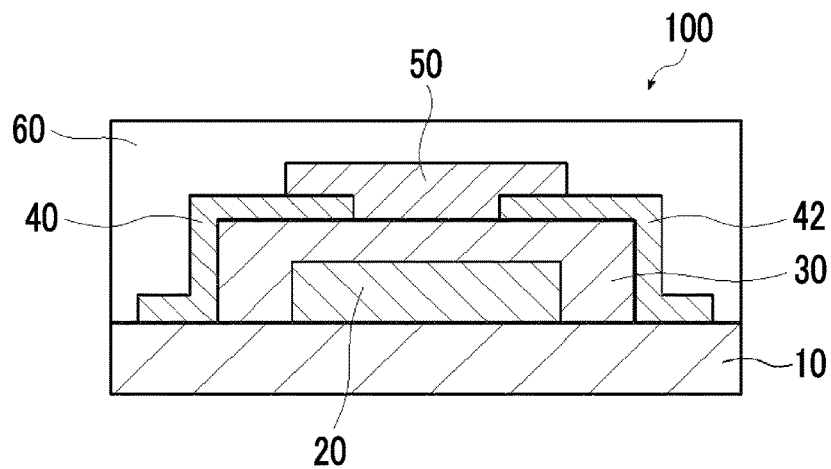
FIG. 1 is a cross-sectional view schematically illustrating a bottom contact type organic thin film transistor according to one embodiment of the present invention.

Hereinafter, the present invention will be described in detail.

In the present specification, the numerical range expressed by using "to" means a range including numerical values described before and after "to" as a lower limit value and an upper limit value.

In the present specification, in a case where there is no description regarding whether a group (atomic group) is substituted or unsubstituted, the group includes both of a group having a substituent and a group not having a substituent. For example, an "alkyl group" includes not only an alkyl group not having a substituent (unsubstituted alkyl group) but also an alkyl group having a substituent (substituted alkyl group).

In the present specification, a combination of preferable aspects is a more preferable aspect.

[Organic Thin Film Transistor]

An organic thin film transistor according to the present invention has an organic semiconductor film containing a compound represented by Formula (1).

Since the compound represented by Formula (1) has a perylene diimide skeleton, the compound represented by Formula (1) is also referred to as a "specific perylene diimide compound" in the present specification.

The specific perylene diimide compound has excellent solubility to an organic solvent, and an organic thin film transistor having an organic semiconductor film manufactured by using this has excellent carrier mobility. This is because of the following reasons.

That is, with respect to the compound having a perylene diimide skeleton, it is known that, a perylene diimide skeleton which is a main skeleton thereof has a symmetric structure, and the compound is used as an n-type organic semiconductor material.

However, the present inventors have conducted research on a compound having a perylene diimide skeleton and have found that, even in a case where at least one portion corresponding to an oxygen atom of an imide skeleton is substituted with a sulfur atom, a selenium-e atom as in the compound (specifically, Comparative Compound 2 in the section of Example below) having a perylene diimide skeleton disclosed in claim 1 of JP2013-515785A, the carrier mobility of the organic thin film transistor manufactured by using this is not sufficient, and solubility to the organic solvent is insufficient.

The present inventors have conducted research on these problems, specific reasons thereof are not revealed. However, it has been found that, it is possible to obtain an organic thin film transistor in which solubility to an organic solvent is improved and carrier mobility is excellent, by breaking symmetry of a perylene diimide skeleton, that is, by using a specific perylene diimide compound in which a ring structure ("Z" of Formula (1)) was introduced to a portion of the perylene diimide skeleton such that a main skeleton became asymmetric.

<Compound Represented by Formula (1)>

A compound (specific perylene diimide compound) represented by Formula (1) is included in an organic semiconductor film of an organic thin film transistor.

The compound represented by Formula (1) is a novel compound, and can be suitably used in an organic semiconductor film of an organic thin film transistor, and also can be used in other applications described below.

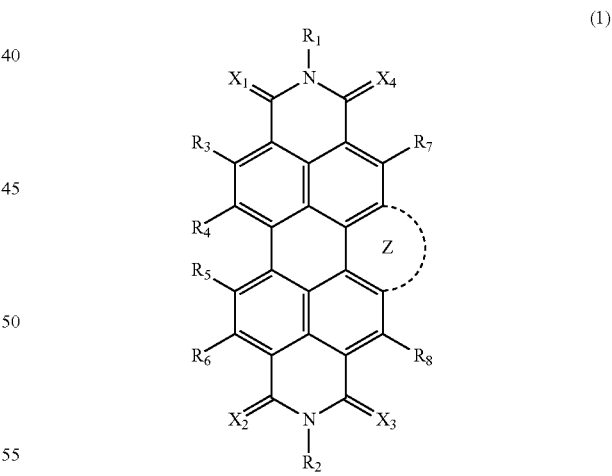

In Formula (1), $R_1$ and $R_2$ each independently represent a hydrogen atom, an alkyl group, an alkenyl group, an alkoxy group, an alkynyl group, a halogenated alkyl group, an aryl group, and a heteroaryl group. These groups may have a substituent.

In the present specification unless described otherwise, an "alkyl group" and an "alkenyl group" have any one of a straight chain shape, a branched shape, and a cyclic shape. Examples of the cyclic alkyl group include a cycloalkyl group, a bicycloalkyl group, and a tricycloalkyl group.

Examples of the cyclic alkenyl group include a cycloalkenyl group and a bicycloalkenyl group.

Examples of a hetero atom included in a "heteroaryl group" in the present specification include a sulfur atom (S), an oxygen atom (O), and a nitrogen atom (N).

Among these, $R_1$ and $R_2$ each independently and preferably represent an alkyl group, an alkenyl group, an alkoxy group, an alkynyl group, a halogenated alkyl group, an aryl group, or a heteroaryl group, more preferably an alkyl group, a halogenated alkyl group, or an aryl group, and even more preferably an alkyl group. Among these alkyl groups, $R_1$ and $R_2$ are preferably a branched alkyl group or a cyclic alkyl group, more preferably a branched alkyl group or a cycloalkyl group having 5 or 6 carbon atoms, and even more preferably a branched alkyl group. Accordingly, solubility to the organic solvent tends to increase.

The number of carbon atoms included in $R_1$ and the number of carbon atoms included in $R_2$ are each independently and preferably 30 or less (preferably 5 to 30 and more preferably 10 to 30). In a case where the number of carbon atoms included in $R_1$ and the number of carbon atoms included in $R_2$ each are 30 or less, carrier mobility of the organic thin film transistor is increased. In a case where the numbers each are 5 or greater, solubility to the organic solvent increases.

$R_1$ and $R_2$ are preferably the same groups. Accordingly, the overlapping of the orbits between molecules of the structure of the compound represented by Formula (1) is improved, and the carrier mobility of the organic thin film transistor is improved.

Examples of the substituent include a halogen atom, an alkyl group, an aryl group, a heterocyclic group (which may be referred to as a heterocyclic group), a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, carbamoyl group, an arylazo group, a heterocyclic azo group, an imide group, a phosphino group, a phosphinyl group, a phosphinyloxy group, a phosphinylamino group, a phosphono group, a silyl group, a hydrazino group, a ureido group, a boronic acid group (—B(OH)$_2$), a phosphato group (—OPO(OH)$_2$), a sulfato group (—OSO$_3$H), and other well-known substituents. The substituent may be further substituted with a substituent.

$R_3$, $R_4$, $R_5$, $R_6$, $R_7$, and $R_8$ each independently represent a hydrogen atom, an alkyl group, an alkenyl group, an alkoxy group, an alkynyl group, a halogenated alkyl group, an aryl group, a heteroaryl group, a halogen atom, a nitro group, and a cyano group.

$R_3$ and $R_4$ may form a ring. In a case where $R_3$ and $R_4$ form a ring, $R_3$ and $R_4$ may be directly bonded to form a ring, or $R_3$ and $R_4$ may form a ring via a divalent substituent.

$R_5$ and $R_6$ may form a ring. In a case where $R_5$ and $R_6$ form a ring, $R_5$ and $R_6$ may be directly bonded to form a ring, or $R_5$ and $R_6$ may form a ring via a divalent substituent.

$R_3$ to $R_8$ each independently and preferably represent a hydrogen atom, a cyano group, a halogen atom, a trifluoromethyl group, and a nitro group, more preferably a hydrogen atom, a cyano group, and a halogen atom, and particularly preferably a hydrogen atom. Accordingly, the film quality is improved, and the carrier mobility is improved.

In view of improvement of the carrier mobility of the organic thin film transistor, $R_3$ and $R_6$ are preferably the same groups. In the same point of view, $R_4$ and $R_5$ are preferably the same groups. In the same point of view, $R_7$ and $R_8$ are preferably the same groups.

Examples of the divalent substituent include a divalent linking group such as —O—, —S—, —NR$_X$—, —CO—, —SO—, or —SO$_2$—, or a divalent linking group obtained by combining two or more of these divalent linking groups. Among these, —O—, —S—, —NR$_X$—, —CO—, —O—CO—, —CO—O—, —NR$_X$—CO—, —CO—NR$_X$—, —O—CO—O—, —NR$_X$—CO—O—, —O—CO—NR$_X$—, or —NR$_X$—CO—NR$_X$— is preferable, —O—, —S—, —NR$_X$—, —CO—, —O—CO—, or —CO—O— is more preferable.

$R_X$'s each independently represent a hydrogen atom, an alkyl group, an alkenyl group, an alkynyl group, an aryl group, or a heteroaryl group, is preferably a hydrogen atom, an alkyl group, or an aryl group, more preferably a hydrogen atom or an alkyl group, and even more preferably an alkyl group having 1 to 8 carbon atoms. $R_X$ may further have a substituent, and the definition of the substituent is as described in $R_1$ and $R_2$.

Z represents a ring structure of a single ring or a fused ring, the number of atoms forming this ring structure is 5 or greater, and four or more of the atoms forming the ring structure are carbon atoms. Z may have a substituent, and the definition of the substituent is as described above. The atom of forming the ring structure includes the four carbon atoms represented by arrows in the following formula.

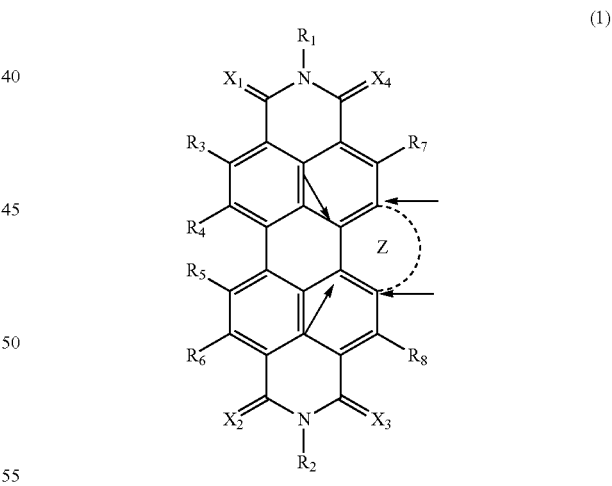

(1)

Here, the atom forming the ring structure may be an atom that is directly bonded for forming the ring. For example, in a case where Z is thiophene, the number of atoms forming the ring structure is 5, and the number of the carbon atoms among the atoms forming the ring structure is 4.

Z represents a ring structure which is a single ring or a fused ring. However, in view of improvement of the carrier mobility of the organic thin film transistor, a single ring is more preferable.

The number of atoms forming the ring structure is 5 or greater, preferably 5 to 20, more preferably 5 to 12, even more preferably 5 to 6 (that is, the ring structure is a single ring, and a 5-membered ring or a 6-membered ring), and particularly preferably 5.

The number of carbon atoms forming the ring structure is 4 or greater, preferably 4 to 20, more preferably 4 to 11, even more preferably 4 to 5, and particularly preferably 4.

Z may be aromatic or nonaromatic. Specifically, an aromatic hydrocarbon ring, a heterocyclic ring, or a fused ring formed by combining these is preferable. These rings may have further a substituent, and the definition of the substituent is as described in $R_1$ and $R_2$.

Examples of the aromatic hydrocarbon ring include a benzene ring, a naphthalene ring, an anthracene ring, a phenanthrene ring, a perylene ring, a tetracene ring, a pyrene ring, a benzopyrene ring, a chrysene ring, a triphenylene ring, a fluorene ring, and a fluoranthene ring.

Examples of the heterocyclic ring include a furan ring, a benzofuran ring, a thiophene ring, a benzothiophene ring, a pyrrole ring, a selenophene ring, a telluropyran ring, a pyrazole ring, an imidazole ring, an oxadiazole ring, an indole ring, a carbazole ring, a benzoxazole ring, a benzothiazole ring, a benzimidazole ring, a pyridine ring, a pyrazine ring, a pyridazine ring, a pyrimidine ring, a triazine ring, a quinoline ring, an isoquinoline ring, a quinoxaline ring, a perimidine ring, a quinazoline ring, a pyran ring, a chromene ring, a thiopyran ring, a thiochromene ring, a selenopyran ring, a selenochromene ring, a telluropilane ring, and a tellurochromene ring.

Among these, Z is preferably a heterocyclic ring and more preferably a heterocyclic ring of a single ring. Among the heterocyclic rings of the single ring, a furan ring, a thiophene ring, a selenophene ring, or a tellurophene ring is preferable, a furan ring, a thiophene ring, or a selenophene ring is more preferable, and a thiophene ring is even more preferable.

$X_1$, $X_2$, $X_3$, and $X_4$ (that is, $X_1$ to $X_4$) each independently represent an oxygen atom, a sulfur atom, a selenium atom, or a tellurium atom. At least one of $X_1$ to $X_4$ is a sulfur atom or a selenium atom. Accordingly, carrier mobility of the organic thin film transistor becomes excellent.

At least one of $X_1$ to $X_4$ is a sulfur atom or a selenium atom. However, in view of improvement of the carrier mobility of the organic thin film transistor, a sulfur atom is preferable.

It is preferable that at least two of $X_1$ to $X_4$ are different atoms. That is, all of $X_1$ to $X_4$ are not the same atoms. For example, in a case where $X_1$ is a sulfur atom, at least one of $X_2$ to $X_4$ is an atom other than a sulfur atom. Accordingly, solubility to the organic solvent of the compound represented by Formula (1) tends to improve. It is assumed that, the reason is because the deviation of a dipole moment in a molecule (deviation of a charge) becomes large in the compound represented by Formula (1).

In view of improvement of the solubility, and improvement of the carrier mobility of the organic thin film transistor, the compound represented by Formula (1) is preferably a compound represented by Formula (2).

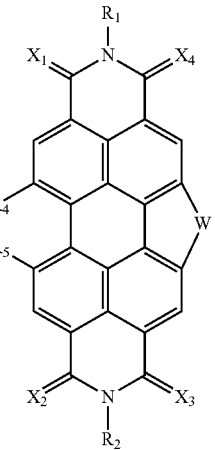

(2)

In Formula (2), $R_1$ and $R_2$ are the same groups, and are alkyl groups having 30 or more carbon atoms. The preferable aspect of $R_1$ and $R_2$ in Formula (2) is the same as that of $R_1$ and $R_2$ in Formula (1).

In Formula (2), $R_4$ and $R_5$ each have the same meaning as $R_4$ and $R_5$ in Formula (1). $R_4$ and $R_5$ are the same groups. The preferable aspect of $R_4$ and $R_5$ in Formula (2) is the same as that of $R_4$ and $R_5$ in Formula (1).

In Formula (2), W represents an oxygen atom, a sulfur atom, a selenium atom, and a tellurium atom. Among these, W is preferably an oxygen atom, a sulfur atom, or a selenium atom and more preferably a sulfur atom.

In Formula (2), $X_1$, $X_2$, $X_3$, and $X_4$ each have the same meaning as $X_1$, $X_2$, $X_3$, and $X_4$ in Formula (1). It is preferable that at least two of $X_1$ to $X_4$ are different atoms. The preferable aspects of $X_1$ to $X_4$ in Formula (2) are the same as those of $X_1$ to $X_4$ in Formula (1).

Specific examples of the compound represented by Formula (1) are provided below.

In the above table, the numerical value on the right of each atom in the description of $R_1$ and $R_2$ represents the number of the atoms. For example, "CH2C3F7" means a "$CH_2C_3F_7$" group.

TABLE 1

| Specific Example | X1 | X2 | X3 | X4 | R1 | R2 | R3 | R4 | R5 | R6 | R7 | R8 | Z |
|---|---|---|---|---|---|---|---|---|---|---|---|---|---|
| 1 | S | O | S | O | n-C4H9 | n-C4H9 | H | H | H | H | H | H | thiophene |
| 2 | S | S | O | O | n-C4H9 | n-C4H9 | H | H | H | H | H | H | thiophene |
| 3 | S | S | S | O | n-C4H9 | n-C4H9 | H | H | H | H | H | H | thiophene |

TABLE 1-continued
| Specific Example | X1 | X2 | X3 | X4 | R1 | R2 | R3 | R4 | R5 | R6 | R7 | R8 | Z |
|---|---|---|---|---|---|---|---|---|---|---|---|---|---|
| 4 | S | O | S | O | n-C6H13 | n-C6H13 | H | H | H | H | H | H |  |
| 5 | S | S | O | O | n-C6H13 | n-C6H13 | H | H | H | H | H | H |  |
| 6 | S | S | S | O | n-C6H13 | n-C6H13 | H | H | H | H | H | H |  |
| 7 | S | O | S | O | n-C10H21 | n-C10H21 | H | H | H | H | H | H |  |
| 8 | S | S | O | O | n-C10H21 | n-C10H21 | H | H | H | H | H | H |  |
| 9 | S | S | S | O | n-C10H21 | n-C10H21 | H | H | H | H | H | H |  |
| 10 | S | O | S | O | 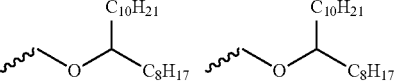 | 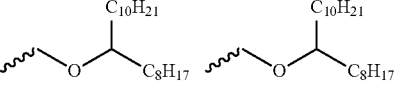 | H | H | H | H | H | H |  |
| 11 | S | S | O | O | 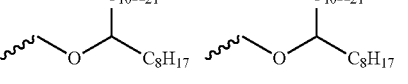 | 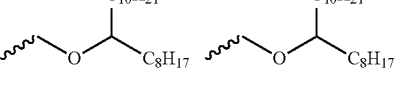 | H | H | H | H | H | H |  |
| 12 | S | S | S | O | 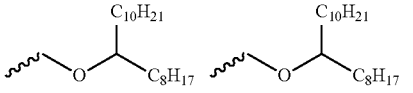 | 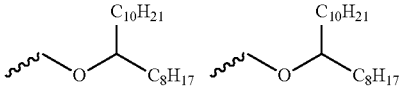 | H | H | H | H | H | H |  |
| 13 | S | O | S | O | n-CH2C3F7 | n-CH2C3F7 | H | H | H | H | H | H |  |
| 14 | S | S | O | O | n-CH2C3F7 | n-CH2C3F7 | H | H | H | H | H | H |  |
| 15 | S | S | S | O | n-CH2C3F7 | n-CH2C3F7 | H | H | H | H | H | H |  |
| 16 | S | O | S | O | 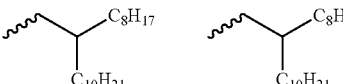 | 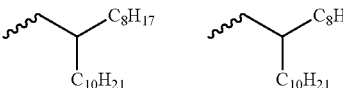 | H | H | H | H | H | H |  |
| 17 | S | S | O | O | 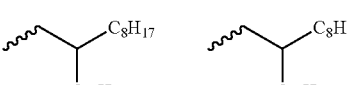 | 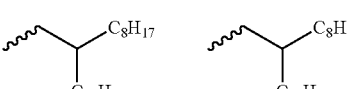 | H | H | H | H | H | H |  |
| 18 | S | S | S | O | 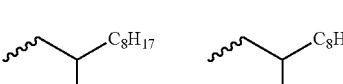 | 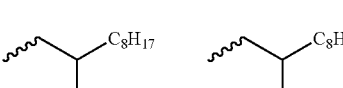 | H | H | H | H | H | H |  |

TABLE 2

| | | | | | | | | | | | | | |
|---|---|---|---|---|---|---|---|---|---|---|---|---|---|
| 19 | S | O | S | O | propenyl | propenyl | H | H | H | H | H | H | thiophene |
| 20 | S | O | S | O | ethynyl | ethynyl | H | H | H | H | H | H | thiophene |
| 21 | S | O | S | O | cyclopentyl | cyclopentyl | H | H | H | H | H | H | thiophene |
| 22 | S | S | O | O | cyclopentyl | cyclopentyl | H | H | H | H | H | H | thiophene |
| 23 | S | O | S | O | cyclohexyl | cyclohexyl | H | H | H | H | H | H | thiophene |
| 24 | S | S | O | O | cyclohexyl | cyclohexyl | H | H | H | H | H | H | thiophene |
| 25 | S | S | S | O | cyclohexyl | cyclohexyl | H | H | H | H | H | H | thiophene |
| 26 | S | O | S | O | phenyl | phenyl | H | H | H | H | H | H | thiophene |
| 27 | S | S | O | O | phenyl | phenyl | H | H | H | H | H | H | thiophene |
| 28 | S | O | S | O | 2,6-dimethylphenyl | 2,6-dimethylphenyl | H | H | H | H | H | H | thiophene |
| 29 | S | S | O | O | 2,6-dimethylphenyl | 2,6-dimethylphenyl | H | H | H | H | H | H | thiophene |
| 30 | S | S | S | O | 2,6-dimethylphenyl | 2,6-dimethylphenyl | H | H | H | H | H | H | thiophene |
| 31 | S | O | S | O | 4-(2-octyl-decyloxy)phenyl | 4-(2-octyl-decyloxy)phenyl | H | H | H | H | H | H | thiophene |

TABLE 2-continued
| 32 | S | S | O | O | 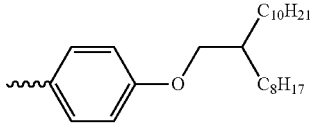 | 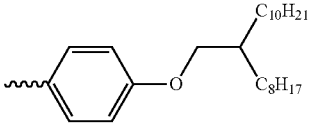 | H | H | H | H | H | H |  |
| 33 | S | O | S | O | 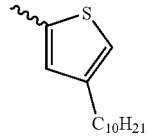 | 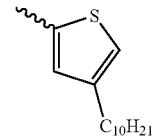 | H | H | H | H | H | H |  |
| 34 | S | S | O | O | 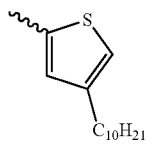 | 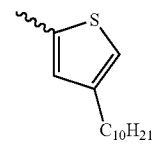 | H | H | H | H | H | H |  |
| 35 | S | O | S | O | 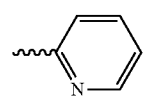 | 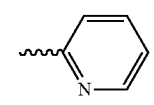 | H | H | H | H | H | H |  |
| 36 | S | S | O | O | 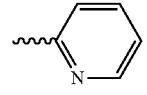 | 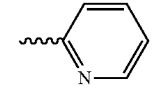 | H | H | H | H | H | H |  |
TABLE 3
| 37 | Se | O  | Se | O | n-C4H9     | n-C4H9     | H | H | H | H | H | H |  |
| 38 | Se | Se | O  | O | n-C4H9     | n-C4H9     | H | H | H | H | H | H |  |
| 39 | Se | O  | Se | O | n-C6H13    | n-C6H13    | H | H | H | H | H | H |  |
| 40 | Se | Se | O  | O | n-C6H13    | n-C6H13    | H | H | H | H | H | H |  |
| 41 | Se | O  | Se | O | n-C10H21   | n-C10H21   | H | H | H | H | H | H |  |
| 42 | Se | Se | O  | O | n-C10H21   | n-C10H21   | H | H | H | H | H | H |  |
| 43 | Se | O  | Se | O | 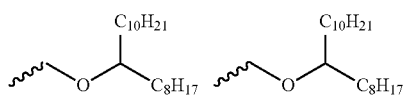 | 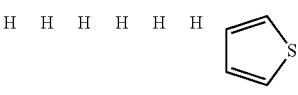 | H | H | H | H | H | H |  |
| 44 | Se | Se | O  | O | 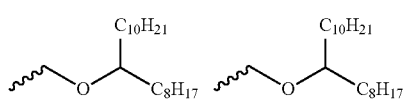 | 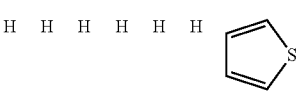 | H | H | H | H | H | H |  |
| 45 | Se | O  | Se | O | n-CH2C3F7  | n-CH2C3F7  | H | H | H | H | H | H |  |

TABLE 3-continued
| 46 | Se | Se | O | O | n-CH2C3F7 | n-CH2C3F7 | H | H | H | H | H | H |  |
| 47 | Se | O | Se | O | 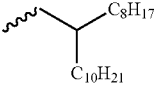 | 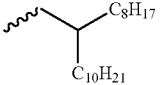 | H | H | H | H | H | H |  |
| 48 | Se | Se | O | O | 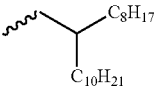 | 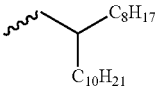 | H | H | H | H | H | H |  |
| 49 | Se | O | Se | O | 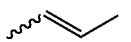 | 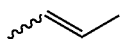 | H | H | H | H | H | H |  |
| 50 | Se | O | Se | O |  |  | H | H | H | H | H | H |  |
TABLE 4
| 51 | Se | O | Se | O |  |  | H | H | H | H | H | H |  |
| 52 | Se | Se | O | O |  | 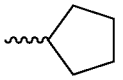 | H | H | H | H | H | H |  |
| 53 | Se | O | Se | O | 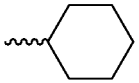 | 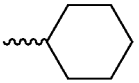 | H | H | H | H | H | H |  |
| 54 | Se | Se | O | O | 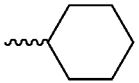 | 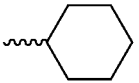 | H | H | H | H | H | H |  |
| 55 | Se | O | Se | O | 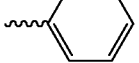 | 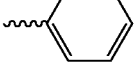 | H | H | H | H | H | H |  |
| 56 | Se | Se | O | O | 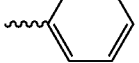 | 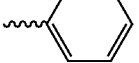 | H | H | H | H | H | H |  |
| 57 | Se | O | Se | O | 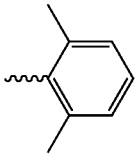 | 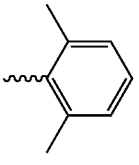 | H | H | H | H | H | H |  |
| 58 | Se | Se | O | O | 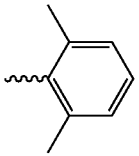 | 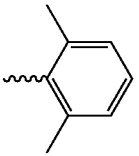 | H | H | H | H | H | H |  |

TABLE 4-continued

| # | | | | | R1 | R2 | | | | | | | Ar |
|---|---|---|---|---|---|---|---|---|---|---|---|---|---|
| 59 | Se | O | Se | O | 4-(2-octyl-decyloxy)phenyl | 4-(2-octyl-decyloxy)phenyl | H | H | H | H | H | H | thienyl |
| 60 | Se | Se | O | O | 4-(2-octyl-decyloxy)phenyl | 4-(2-octyl-decyloxy)phenyl | H | H | H | H | H | H | thienyl |
| 61 | Se | O | Se | O | 4-decyl-thiophen-2-yl | 4-decyl-thiophen-2-yl | H | H | H | H | H | H | thienyl |
| 62 | Se | Se | O | O | 4-decyl-thiophen-2-yl | 4-decyl-thiophen-2-yl | H | H | H | H | H | H | thienyl |
| 63 | Se | O | Se | O | pyridin-2-yl | pyridin-2-yl | H | H | H | H | H | H | |
| 64 | Se | Se | O | O | pyridin-2-yl | pyridin-2-yl | H | H | H | H | H | H | thienyl |

TABLE 5

| # | | | | | R1 | R2 | | | | | | | Ar |
|---|---|---|---|---|---|---|---|---|---|---|---|---|---|
| 65 | S | O | S | O | n-C4H9 | n-C4H9 | Cl | H | Cl | H | H | H | thienyl |
| 66 | S | S | O | O | n-C4H9 | n-C4H9 | Cl | H | Cl | H | H | H | thienyl |
| 67 | S | O | S | O | n-C6H13 | n-C6H13 | Cl | H | Cl | H | H | H | thienyl |
| 68 | S | S | O | O | n-C6H13 | n-C6H13 | Cl | H | Cl | H | H | H | thienyl |
| 69 | S | O | S | O | n-C10H21 | n-C10H21 | Cl | H | Cl | H | H | H | thienyl |
| 70 | S | S | O | O | n-C10H21 | n-C10H21 | Cl | H | Cl | H | H | H | thienyl |
| 71 | S | O | S | O | 2-octyl-decyloxymethyl | 2-octyl-decyloxymethyl | Cl | H | Cl | H | H | H | thienyl |

TABLE 5-continued
| | | | | | | | | | | | | | |
|---|---|---|---|---|---|---|---|---|---|---|---|---|---|
| 72 | S | S | O | O | 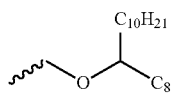 | 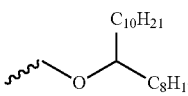 | Cl | H | Cl | H | H | H |  |
| 73 | S | O | S | O | n-CH2C3F7 | n-CH2C3F7 | Cl | H | Cl | H | H | H |  |
| 74 | S | S | O | O | n-CH2C3F7 | n-CH2C3F7 | Cl | H | Cl | H | H | H |  |
| 75 | S | O | S | O |  | 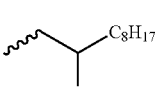 | Cl | H | Cl | H | H | H |  |
| 76 | S | S | O | O | 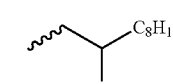 | 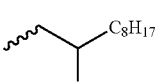 | Cl | H | Cl | H | H | H |  |
| 77 | S | O | S | O | 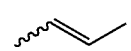 | 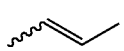 | Cl | H | Cl | H | H | H |  |
| 78 | S | O | S | O |  |  | Cl | H | Cl | H | H | H |  |
TABLE 6
| | | | | | | | | | | | | | |
|---|---|---|---|---|---|---|---|---|---|---|---|---|---|
| 79 | S | O | S | O |  |  | Cl | H | Cl | H | H | H |  |
| 80 | S | S | O | O |  |  | Cl | H | Cl | H | H | H |  |
| 81 | S | O | S | O |  |  | Cl | H | Cl | H | H | H |  |
| 82 | S | S | O | O | 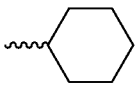 |  | Cl | H | Cl | H | H | H |  |
| 83 | S | O | S | O | 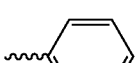 | 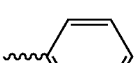 | Cl | H | Cl | H | H | H |  |
| 84 | S | S | O | O | 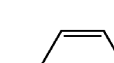 | 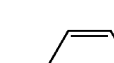 | Cl | H | Cl | H | H | H |  |
| 85 | S | O | S | O | 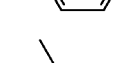 | 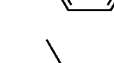 | Cl | H | Cl | H | H | H |  |

TABLE 6-continued
| | | | | | | | | | | | | | | |
|---|---|---|---|---|---|---|---|---|---|---|---|---|---|---|
| 86 | S | S | O | O | 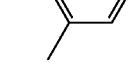 | 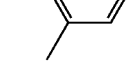 | Cl | H | Cl | H | H | H |  |
| 87 | S | O | S | O | 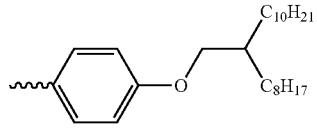 | 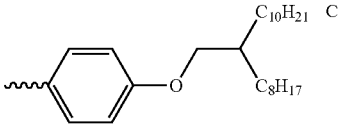 | Cl | H | Cl | H | H | H |  |
| 88 | S | S | O | O | 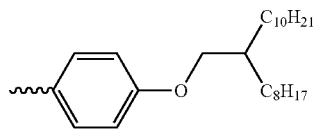 | 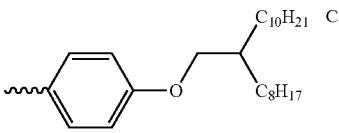 | Cl | H | Cl | H | H | H |  |
| 89 | S | O | S | O | 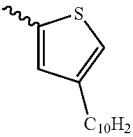 | 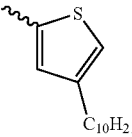 | Cl | H | Cl | H | H | H |  |
| 90 | S | S | O | O | 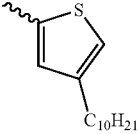 | 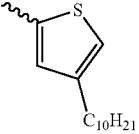 | Cl | H | Cl | H | H | H |  |
| 91 | S | O | S | O | 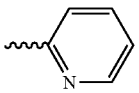 | 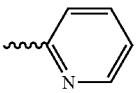 | Cl | H | Cl | H | H | H |  |
| 92 | S | S | O | O | 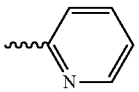 | 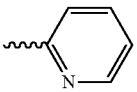 | Cl | H | Cl | H | H | H |  |
TABLE 7
| | | | | | | | | | | | | | |
|---|---|---|---|---|---|---|---|---|---|---|---|---|---|
| 93 | S | O | S | O | n-C4H9 | n-C4H9 | F | H | F | H | H | H |  |
| 94 | S | S | O | O | n-C4H9 | n-C4H9 | F | H | F | H | H | H |  |
| 95 | S | O | S | O | n-C6H13 | n-C6H13 | F | H | F | H | H | H |  |
| 96 | S | S | O | O | n-C6H13 | n-C6H13 | F | H | F | H | H | H |  |
| 97 | S | O | S | O | n-C10H21 | n-C10H21 | F | H | F | H | H | H |  |

TABLE 7-continued
| | | | | | | | | | | | | | |
|---|---|---|---|---|---|---|---|---|---|---|---|---|---|
| 98 | S | S | O | O | n-C10H21 | n-C10H21 | F | H | F | H | H | H |  |
| 99 | S | O | S | O | 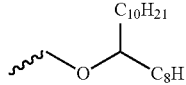 | 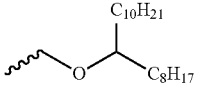 | F | H | F | H | H | H |  |
| 100 | S | S | O | O | 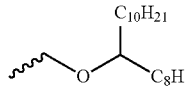 | 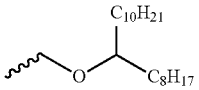 | F | H | F | H | H | H |  |
| 101 | S | O | S | O | n-CH2C3F7 | n-CH2C3F7 | F | H | F | H | H | H |  |
| 102 | S | S | O | O | n-CH2C3F7 | n-CH2C3F7 | F | H | F | H | H | H |  |
| 103 | S | O | S | O | 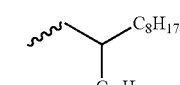 | 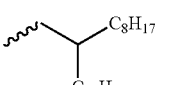 | F | H | F | H | H | H |  |
| 104 | S | S | O | O | 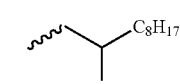 | 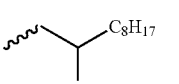 | F | H | F | H | H | H |  |
| 105 | S | O | S | O | 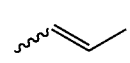 | 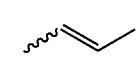 | F | H | F | H | H | H |  |
| 106 | S | O | S | O |  |  | F | H | F | H | H | H |  |
TABLE 8
| | | | | | | | | | | | | | |
|---|---|---|---|---|---|---|---|---|---|---|---|---|---|
| 107 | S | O | S | O |  | 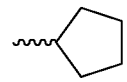 | F | H | F | H | H | H |  |
| 108 | S | S | O | O | 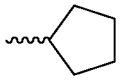 | 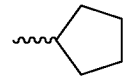 | F | H | F | H | H | H |  |
| 109 | S | O | S | O | 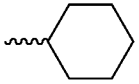 |  | F | H | F | H | H | H |  |
| 110 | S | S | O | O |  |  | F | H | F | H | H | H |  |
| 111 | S | O | S | O | 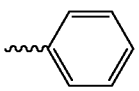 | 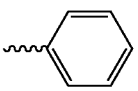 | F | H | F | H | H | H |  |
| 112 | S | S | O | O | 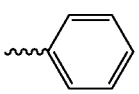 | 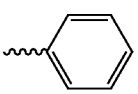 | F | H | F | H | H | H |  |

TABLE 8-continued
| 113 | S | O | S | O | 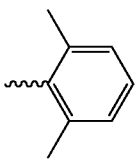 | 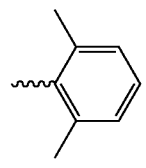 | F | H | F | H | H | H |  |
| 114 | S | S | O | O | 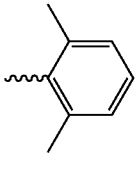 | 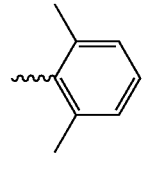 | F | H | F | H | H | H |  |
| 115 | S | O | S | O | 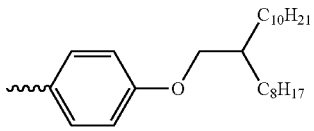 | 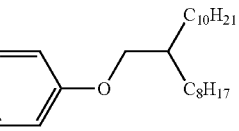 | F | H | F | H | H | H |  |
| 116 | S | S | O | O | 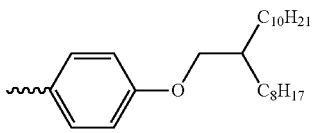 | 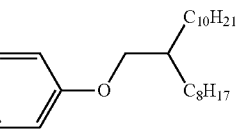 | F | H | F | H | H | H |  |
| 117 | S | O | S | O | 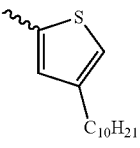 | 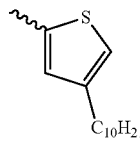 | F | H | F | H | H | H |  |
| 118 | S | S | O | O | 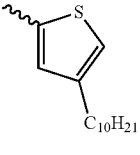 | 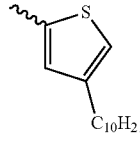 | F | H | F | H | H | H |  |
| 119 | S | O | S | O | 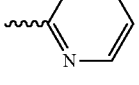 | 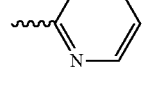 | F | H | F | H | H | H |  |
| 120 | S | S | O | O | 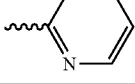 | 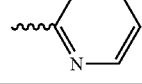 | F | H | F | H | H | H |  |
TABLE 9
| 121 | S | O | S | O | n-C4H9 | n-C4H9 | CN | H | CN | H | H | H |  |
| 122 | S | S | O | O | n-C4H9 | n-C4H9 | CN | H | CN | H | H | H |  |
| 123 | S | O | S | O | n-C6H13 | n-C6H13 | CN | H | CN | H | H | H |  |
| 124 | S | S | O | O | n-C6H13 | n-C6H13 | CN | H | CN | H | H | H |  |

TABLE 9-continued
| 125 | S | O | S | O | n-C10H21 | n-C10H21 | CN | H | CN | H | H | H |  |
| --- | --- | --- | --- | --- | --- | --- | --- | --- | --- | --- | --- | --- | --- |
| 126 | S | S | O | O | n-C10H21 | n-C10H21 | CN | H | CN | H | H | H |  |
| 127 | S | O | S | O | 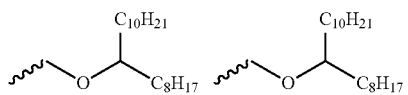 | 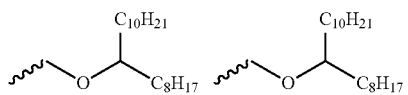 | CN | H | CN | H | H | H |  |
| 128 | S | S | O | O | 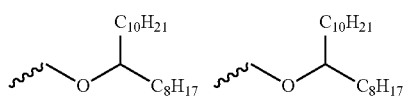 | 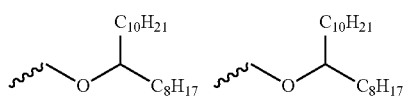 | CN | H | CN | H | H | H |  |
| 129 | S | O | S | O | n-CH2C3F7 | n-CH2C3F7 | CN | H | CN | H | H | H |  |
| 130 | S | S | O | O | n-CH2C3F7 | n-CH2C3F7 | CN | H | CN | H | H | H |  |
| 131 | S | O | S | O | 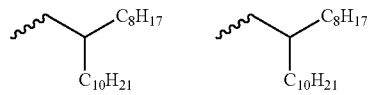 | 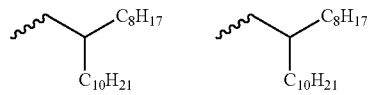 | CN | H | CN | H | H | H |  |
| 132 | S | S | O | O | 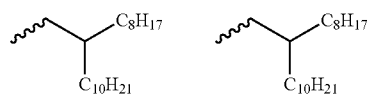 | 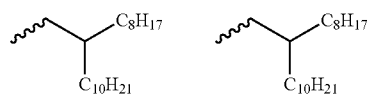 | CN | H | CN | H | H | H |  |
| 133 | S | O | S | O |  |  | CN | H | CN | H | H | H |  |
| 134 | S | O | S | O |  |  | CN | H | CN | H | H | H |  |
TABLE 10
| 135 | S | O | S | O | 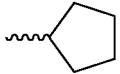 | 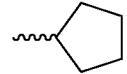 | CN | H | CN | H | H | H |  |
| --- | --- | --- | --- | --- | --- | --- | --- | --- | --- | --- | --- | --- | --- |
| 136 | S | S | O | O |  |  | CN | H | CN | H | H | H |  |
| 137 | S | O | S | O | 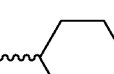 |  | CN | H | CN | H | H | H |  |
| 138 | S | S | O | O | 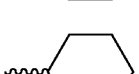 | 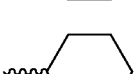 | CN | H | CN | H | H | H |  |
| 139 | S | O | S | O |  |  | CN | H | CN | H | H | H |  |

TABLE 10-continued
| 140 | S | S | O | O | 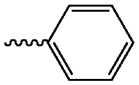 | 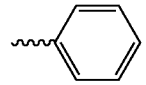 | CN | H | CN | H | H | H |  |
| 141 | S | O | S | O | 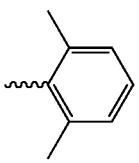 | 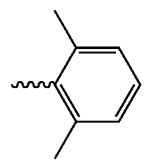 | CN | H | CN | H | H | H |  |
| 142 | S | S | O | O | 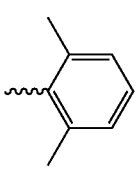 | 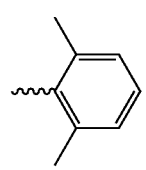 | CN | H | CN | H | H | H |  |
| 143 | S | O | S | O | 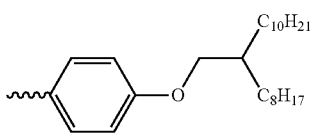 | 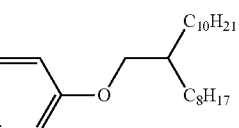 | CN | H | CN | H | H | H |  |
| 144 | S | S | O | O | 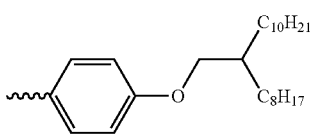 | 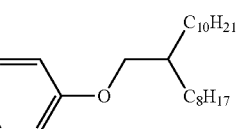 | CN | H | CN | H | H | H |  |
| 145 | S | O | S | O | 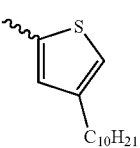 | 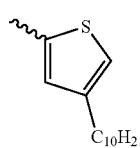 | CN | H | CN | H | H | H |  |
| 146 | S | S | O | O | 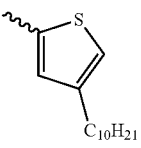 | 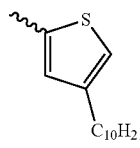 | CN | H | CN | H | H | H |  |
| 147 | S | O | S | O | 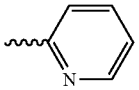 | 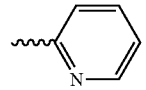 | CN | H | CN | H | H | H |  |
| 148 | S | S | O | O | 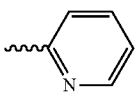 | 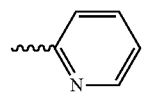 | CN | H | CN | H | H | H |  |
TABLE 11
| 149 | S | O | S | O | n-C10H21 | n-C10H21 | H | H | H | H | H | H |  |
| 150 | S | S | O | O | n-C10H21 | n-C10H21 | H | H | H | H | H | H |  |
| 151 | S | O | S | O | 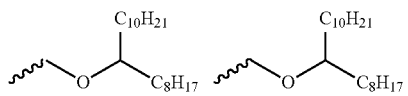 |  | H | H | H | H | H | H |  |

TABLE 11-continued
| 152 | S | S | O | O | 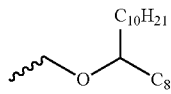 C10H21 C8H17 | 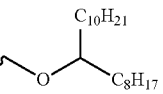 C10H21 C8H17 | H | H | H | H | H | H |  Se |
| 153 | S | O | S | O | n-CH2C3F7 | n-CH2C3F7 | H | H | H | H | H | H |  Se |
| 154 | S | S | O | O | n-CH2C3F7 | n-CH2C3F7 | H | H | H | H | H | H |  Se |
| 155 | S | O | S | O | 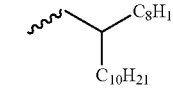 C8H17 C10H21 | 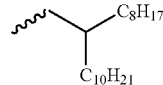 C8H17 C10H21 | H | H | H | H | H | H |  Se |
| 156 | S | S | O | O | 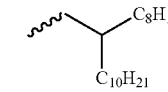 C8H17 C10H21 | 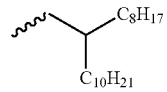 C8H17 C10H21 | H | H | H | H | H | H |  Se |
| 157 | S | O | S | O | 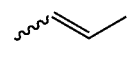 | 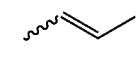 | H | H | H | H | H | H |  Se |
| 158 | S | O | S | O |  |  | H | H | H | H | H | H |  Se |
TABLE 12
| 159 | S | O | S | O | 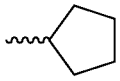 | 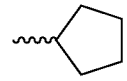 | H | H | H | H | H | H |  Se |
| 160 | S | S | O | O |  |  | H | H | H | H | H | H |  Se |
| 161 | S | O | S | O |  | 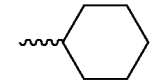 | H | H | H | H | H | H |  Se |
| 162 | S | S | O | O |  |  | H | H | H | H | H | H |  Se |
| 163 | S | O | S | O | 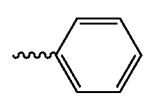 | 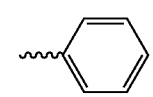 | H | H | H | H | H | H |  Se |
| 164 | S | S | O | O | 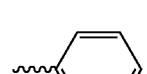 | 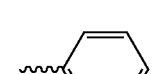 | H | H | H | H | H | H |  Se |
| 165 | S | O | S | O | 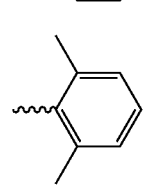 | 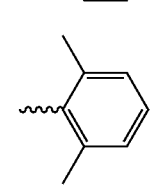 | H | H | H | H | H | H |  Se |

TABLE 12-continued

| # | | | | | Ar1 | Ar2 | R1 | R2 | R3 | R4 | R5 | R6 | Het |
|---|---|---|---|---|---|---|---|---|---|---|---|---|---|
| 166 | S | S | O | O | 2,6-dimethylphenyl | 2,6-dimethylphenyl | H | H | H | H | H | H | selenophene |
| 167 | S | O | S | O | 4-(2-decyl-decyloxy)phenyl* | 4-(2-decyl-decyloxy)phenyl* | H | H | H | H | H | H | selenophene |
| 168 | S | S | O | O | 4-(2-decyl-decyloxy)phenyl* | 4-(2-decyl-decyloxy)phenyl* | H | H | H | H | H | H | selenophene |
| 169 | S | O | S | O | 4-decylthiophen-2-yl | 4-decylthiophen-2-yl | H | H | H | H | H | H | selenophene |
| 170 | S | S | O | O | 4-decylthiophen-2-yl | 4-decylthiophen-2-yl | H | H | H | H | H | H | selenophene |
| 171 | S | O | S | O | pyridin-2-yl | pyridin-2-yl | H | H | H | H | H | H | selenophene |
| 172 | S | S | O | O | pyridin-2-yl | pyridin-2-yl | H | H | H | H | H | H | selenophene |

*aryl group: 4-[(2-octyl)decyloxy... with $C_{10}H_{21}$ and $C_8H_{17}$ branches <Method of Manufacturing Compound Represented by Formula (1)>

The compound represented by Formula (1) can be manufactured (synthesized) with reference to the well-known method. Specific examples of the manufacturing method include a method of stirring a mixture obtained by mixing a compound (for example, synthesis with reference to European Journal Of Organic Chemistry 2000. 2, 365 to 380.) represented by Formula (B1) or (B2), a Lawesson's reagent, and an organic solvent, at a predetermined temperature (for example, about 100° C. to 200° C.) for a predetermined time (for example, about 0.5 to 5 hours).

The organic solvent used in the synthesis is not particularly limited. However, for example, 1-methylnaphthalene, tetralin, mesitylene, and xylene can be used.

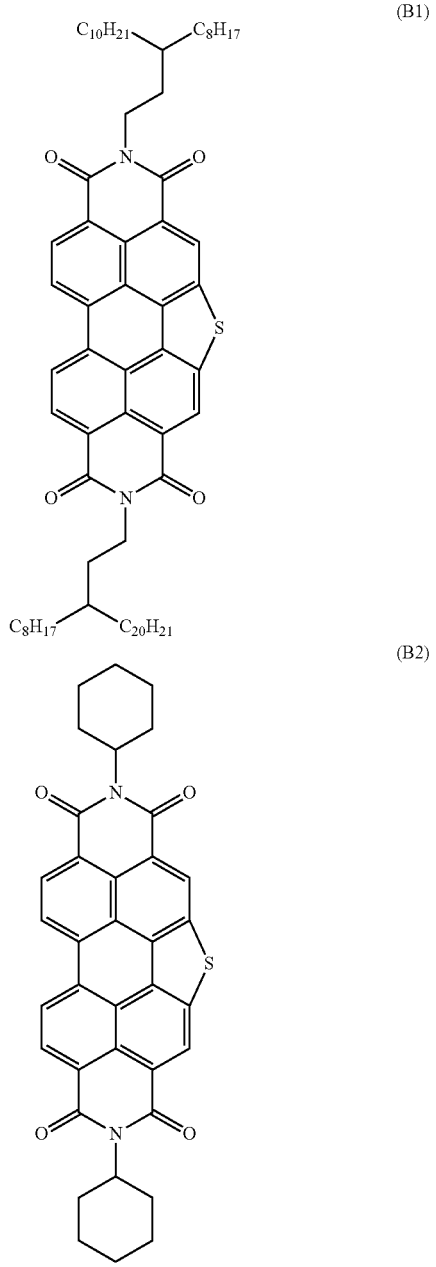

<Structure of Organic Thin Film Transistor and Method of Manufacturing Organic Thin Film Transistor>

Subsequently, a structure of the organic thin film transistor according to the present invention in which the compound (specific perylene diimide compound) represented by Formula (1) is used in the organic semiconductor film of the organic thin film transistor and a manufacturing method thereof are described.

The organic thin film transistor according to the present invention may have an organic semiconductor film (organic semiconductor layer) including a compound represented by Formula (1) and may further have a source electrode, a drain electrode, and a gate electrode.

The structure of the organic thin film transistor according to the present embodiment is not particularly limited. For example, the structure thereof may have any one of a bottom contact type (bottom contact-bottom gate type and bottom contact-top gate type) and top contact type (top contact-bottom gate type and top contact-top gate type).

Hereinafter, an example of the organic thin film transistor according to the present invention is described with reference to the drawings.

FIG. 1 is a cross-sectional view schematically illustrating a bottom contact type organic thin film transistor 100 according to one embodiment of the present invention.

In the example of FIG. 1, the organic thin film transistor 100 has a substrate 10, a gate electrode 20, a gate insulating film 30, a source electrode 40, a drain electrode 42, an organic semiconductor film (organic semiconductor layer) 50, and a sealing layer 60. Here, the organic semiconductor film 50 is manufactured by using the compound represented by Formula (1).

Hereinafter, each of methods of manufacturing the substrate, the gate electrode, the gate insulating film, the source electrode, the drain electrode, the organic semiconductor film (the organic semiconductor layer), and the sealing layer is specifically described below.

(Substrate)

The substrate plays a role of supporting the gate electrode, the source electrode, the drain electrode, and the like which will be described later.

The type of the substrate is not particularly limited, and examples thereof include a plastic substrate, a glass substrate, and a ceramic substrate. Among these, in view of applicability to each device and costs, a glass substrate or a plastic substrate is preferable.

(Gate Electrode)

Examples of materials of the gate electrode include metal such as gold (Au), silver, aluminum, copper, chromium, nickel, cobalt, titanium, platinum, magnesium, calcium, barium, or sodium; conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium arsenide; and a carbon material such as fullerene, carbon nanotubes, or graphite. Among these, a metal is preferable, and silver and aluminum are more preferable.

The thickness of the gate electrode is not particularly limited but is preferably 20 to 200 nm.

The gate electrode may function as a substrate, and, in this case, the substrate may not be provided.

A method of forming the gate electrode is not particularly limited, but examples thereof include a method of vacuum vapor-depositing or sputtering an electrode material onto a substrate, a method of coating a substrate with a composition for forming an electrode, a method of printing a composition for forming an electrode onto a substrate, and the like. Examples of a patterning method in a case where the electrode is patterned include a photolithography method; a printing method such as ink jet printing, screen printing, offset printing, or relief printing (flexo printing); and a mask vapor deposition method.

(Gate Insulating Film)

Examples of the material of the gate insulating film include a polymer such as polymethyl methacrylate, polystyrene, polyvinyl phenol, polyimide, polycarbonate, polyester, polyvinyl alcohol, polyvinyl acetate, polyurethane, polysulfone, polybenzoxazole, polysilsesquioxane, an epoxy resin, and a phenol resin; oxide such as silicon dioxide, aluminum oxide, and titanium oxide; and nitride such as silicon nitride. Among these materials, in view of the compatibility with the organic semiconductor film, it is preferable that the material of the gate insulating film is a polymer.

The film thickness of the gate insulating film is not particularly limited but is preferably 100 to 1,000 nm.

The method of forming the gate insulating film is not particularly limited, and examples thereof include a method of coating a substrate on which a gate electrode is formed with a composition for forming a gate insulating film and a method of evaporating or sputtering a material of a gate insulating film.

(Source Electrode and Drain Electrode)

Specific examples of the materials of the source electrode and the drain electrode are the same as those of the gate electrode. Among these, a metal is preferable, and silver is more preferable.

The method of forming a source electrode and a drain electrode is not particularly limited, and examples thereof include a method of vacuum-evaporating or sputtering an electrode material on a substrate on which a gate electrode and a gate insulating film are formed and a method of applying or printing an electrode forming composition. Specific examples of the patterning method are the same as those of the gate electrode.

(Organic Semiconductor Film)

The method of manufacturing an organic semiconductor film is not particularly limited, as long as the organic semiconductor film including the compound represented by Formula (1) is manufactured. However, for example, the organic semiconductor film can be manufactured by coating a substrate with an organic thin film transistor composition (described below) including the compound represented by Formula (1) and drying the organic thin film transistor composition.

The expression "coating a substrate with an organic thin film transistor composition" includes an aspect of applying the organic thin film transistor composition over the substrate through an independent layer provided on the substrate, in addition to an aspect of directly applying the organic thin film transistor composition to the substrate.

Well-known methods can be used as the coating method with the organic thin film transistor composition, and examples thereof include a bar coating method, a spin coating method, a knife coating method, a doctor blade method, an ink jet printing method, a flexographic printing method, a gravure printing method, and a screen printing method. As the coating method with the organic thin film transistor composition, a method (so-called gap cast method) of forming an organic semiconductor film disclosed in JP2013-207085A and a method (a so-called edge casting method and a continuous edge casting method) of manufacturing an organic semiconductor thin film disclosed in WO2014/175351A and the like are suitably used.

With respect to drying (a drying treatment), an optimum condition may be suitably selected depending on the types of the respective components included in the organic thin film transistor composition so as to perform natural drying. However, in view of improvement of productivity, a heating treatment is preferably performed. For example, the heating temperature is preferably 30° C. to 150° C. and more preferably 40° C. to 120° C., and the heating time is preferably 10 to 300 minutes and more preferably 20 to 180 minutes.

The film thickness of the manufactured organic semiconductor film is not particularly limited. However, in view of the excellent effect of the present invention, the film thickness is preferably 10 to 500 nm and more preferably 30 to 200 nm.

In this manner, the organic semiconductor film containing the compound represented by Formula (1) is suitably used in the organic thin film transistor. However, the present invention is not limited to this application, and the organic semiconductor film containing the compound represented by Formula (1) can be applied to other applications described below.

(Sealing Layer)

In view of durability, the organic thin film of the present invention preferably includes a sealing layer as an outermost layer. In the sealing layer, a known sealant (sealing layer forming composition) can be used.

The thickness of the sealing layer is not particularly limited, and is preferably 0.2 to 10 µm.

(Other Organic Thin Film Transistors)

Figure 2:
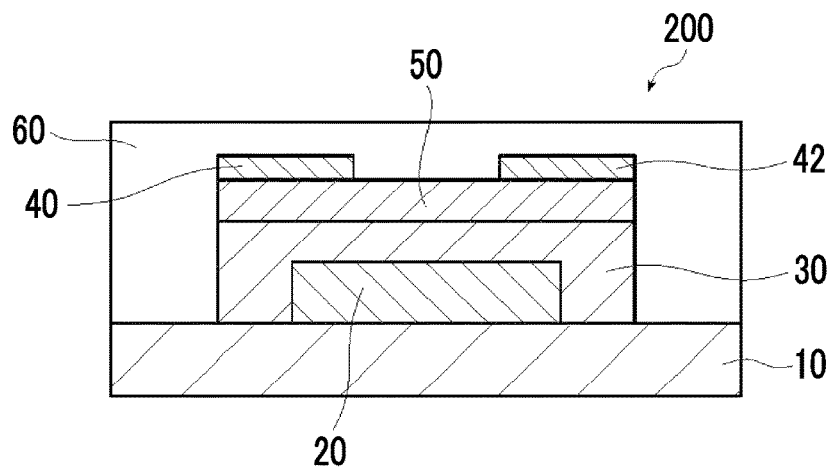
FIG. 2 is a cross-sectional view schematically illustrating a top contact type organic thin film transistor according to one embodiment of the present invention.

FIG. 2 is a cross-sectional view schematically illustrating a top contact type organic thin film transistor 200 according to one embodiment of the present invention.

In the example of FIG. 2, the organic thin film transistor 200 has the substrate 10, the gate electrode 20, the gate insulating film 30, the source electrode 40, the drain electrode 42, the organic semiconductor film (organic semiconductor layer) 50, and the sealing layer 60. Here, the organic semiconductor film 50 is formed by using the organic thin film transistor composition according to the present invention described below.

The substrate, the gate electrode, the gate insulating film, the source electrode, the drain electrode, the organic semiconductor film, and the sealing layer are as described above, and the description thereof is omitted.

(Application of Organic Thin Film Transistor)

The above organic thin film transistor can be applied to a display unit of electronic paper and a display device, which displays an image. Electronic paper and a display device may have well-known structures, and thus the description thereof is omitted.

[Organic Thin Film Transistor Composition]

The organic thin film transistor composition according to the present invention is used in the manufacturing of the organic semiconductor film of the organic thin film transistor.

The organic thin film transistor composition described below may be used in the other uses described below. In this case, the "organic thin film transistor composition" may be simply referred to as an "organic semiconductor composition".

The organic thin film transistor composition contains the compound represented by Formula (1). However, generally, in view of the improvement of the coating properties thereof, the organic thin film transistor composition further contains an organic solvent.

In a case where the organic thin film transistor composition contains an organic solvent, the content of the compound represented by Formula (1) is preferably 0.01 to 20 mass %, more preferably 0.05 to 10 mass %, and even more preferably 0.1 to 5 mass % with respect to the total mass of the organic thin film transistor composition.

<Organic Solvent>

The organic solvent is not particularly limited, and examples thereof include a hydrocarbon solvent such as hexane, octane, and decane, an aromatic hydrocarbon solvent such as toluene, xylene, mesitylene, ethylbenzene, decalin, 1-methylnaphthalene, and tetralin, a ketone solvent such as acetone, methyl ethyl ketone, methyl isobutyl ketone, and cyclohexanone, a halogenated hydrocarbon solvent such as dichloromethane, chloroform, tetrachloromethane, dichloroethane, trichloroethane, tetrachloroethane, chlorobenzene, dichlorobenzene, and chlorotoluene, an ester solvent such as ethyl acetate, butyl acetate, amyl acetate, and ethyl lactate, an alcohol solvent such as methanol, propanol, butanol, pentanol, hexanol, cyclohexanol, methyl cellosolve, ethyl cellosolve, and ethylene glycol, an ether solvent such as butoxybenzene, dibutyl ether, tetrahydrofuran, dioxane, and anisole, an amide solvent such as N,N-dimethylformamide and N,N-dimethylacetamide, an imide solvent such as 1-methyl-2-pyrrolidone and 1-methyl-2-imidazolidinone, a sulfoxide type solvent such as dimethylsulfoxide, and a nitrile solvent such as acetonitrile.

Among these, in view of excellent solubility of the compound represented by Formula (1), butoxybenzene or anisole is preferably used.

The organic solvent may be used singly or two or more kinds thereof may be used in combination.

In a case where the organic solvent is contained, the content thereof is preferably 80 to 99.99 mass %, more preferably 90 to 99.99 mass %, even more preferably 95 to 99.95 mass %, with respect to the total mass of the organic thin film transistor composition.

<Binder Polymer>

The organic thin film transistor composition may further contain a binder polymer.

The types of the binder polymer are not particularly limited, and well-known binder polymers can be used. Examples thereof include a polymer compound such as a polystyrene resin, an acrylic resin, rubber, and a thermoplastic elastomer.

Among these, as the binder polymer, a polymer compound (a polymer having a monomer unit having a benzene ring group) having a benzene ring is preferable. The content of the monomer unit having a benzene ring is not particularly limited. However, the content is preferably 50 mol % or greater, more preferably 70 mol % or greater, and even more preferably 90 mol % or greater with respect to the total monomer unit. The upper limit thereof is not particularly limited, and examples thereof include 100 mol %.

Specific examples of the binder polymer include polystyrene, poly(α-methylstyrene), polyvinyl cinnamate, poly(4-vinylphenyl), and poly(4-methylstyrene).

The weight-average molecular weight of the binder polymer is not particularly limited, but is preferably 1,000 to 2,000,000, more preferably 3,000 to 1,000,000, and still more preferably 5,000 to 600,000. The weight-average molecular weight can be obtained by gel permeation chromatography (GPC).

The content in a case where the binder polymer is contained is preferably 5 to 200 parts by mass, and more preferably 20 to 150 parts by mass with respect to 100 parts by mass of the compound represented by Formula (1) included in the organic thin film transistor composition.

<Other Components>

The organic thin film transistor composition may further contain other components in addition to the above. Examples of the other component include a surfactant and a phenolic reducing agent (a so-called migration inhibitor).

In addition to these components, components included in the organic thin film transistor composition (organic semiconductor composition) in the related art may be contained.

<Preparation Method>

The method of preparing the organic thin film transistor composition is not particularly limited, and well-known methods can be employed. For example, the organic thin film transistor composition according to the present invention can be obtained by adding the compound represented by Formula (1) in the predetermined amount in the organic solvent and suitably performing a stirring treatment.

[Organic Thin Film Transistor Material]

An organic thin film transistor material according to the present invention contains the compound represented by Formula (1). The organic thin film transistor material is used in the organic thin film transistor and refers to a material exhibiting semiconductor characteristics.

The compound represented by Formula (1) is a material exhibiting properties as a semiconductor and is an n-type (electron transporting type) organic semiconductor material which conducts electrons as carriers.

The organic thin film transistor material may be used in the other applications described below. In this case, the "organic thin film transistor material" may be simply referred to as an "organic semiconductor material".

[Other Applications of Compound Represented by Formula (1)]

The compound represented by Formula (1) has excellent properties as described above and thus can be suitably used in other applications in addition to the organic thin film transistor.

Examples of the other applications include a non-luminous organic semiconductor device. The non-luminous organic semiconductor device means a device that is not intended to emit light.

In addition to the organic thin film transistor described above, examples of the non-luminous organic semiconductor device include an organic photoelectric conversion element (individual imaging element for optical sensor application, solar cell for energy conversion, and the like), a gas sensor, an organic rectifying element, an organic inverter, and an information recording element.

The non-luminous organic semiconductor device preferably causes the organic semiconductor film to function as an electronic element. The organic semiconductor film includes an organic semiconductor film including the compound represented by Formula (1).

EXAMPLES

Hereinafter, the organic thin film transistor according to the present invention is specifically described with reference to examples. However, the present invention is not limited thereto.

Example Compounds 1 and 2

Example Compounds 1 and 2 were synthesized according to Scheme (S1).

Scheme (S1)

(B1) → Lawesson's reagent (5.0 eq), 1-methylnaphthalene (50 nM), 180° C. 60 min → (A1) + (A2)

First, a starting material (Formula (B1)) in Scheme (S1) was synthesized with reference to European Journal Of Organic Chemistry 2000. 2, 365 to 380.

Subsequently, the starting material (4.0 g, 3.90 mmol), a Lawesson's reagent (7.90 g, 19.5 mmol), and 80 mL of 1-methylnaphthalene were added, and stirring was performed at 180° C. for one hour.

Thereafter, the reaction liquid was cooled down to the room temperature, purified with column chromatography (toluene:hexane=1:2), so as to obtain Example Compound 1 (63 mg, 1.5%, see Formula (A1)) as a blue solid and Example Compound 2 (454 mg, 11%, see Formula (A2)). The structures of Example Compounds 1 and 2 obtained were identified by $^1$H Nuclear Magnetic Resonance (NMR).

Example Compound 1 $^1$H NMR (CDCl$_3$, 400 MHz) δ: 0.84-1.55 (82H, m), 4.72 (4H, br), 6.70 (2H, br), 7.48 (2H, br), 7.87 (2H, br).

Example Compound 2 $^1$H NMR (CDCl$_3$, 400 MHz) δ: 0.85-1.64 (82H, m), 4.39 (2H, br), 4.85 (2H, br), 7.39 (1H, br), 7.48 (1H, br), 8.03 (1H, br), 8.19 (1H, br), 8.34 (1H, s), 8.39 (1H, s).

Example Compound 3

Example Compound 3 was synthesized according to Scheme (S2).

Scheme (2)

(B3) → Lawesson's reagent (5.0 eq), 1-methylnaphthalene (50 nM), 180° C. 60 min

-continued

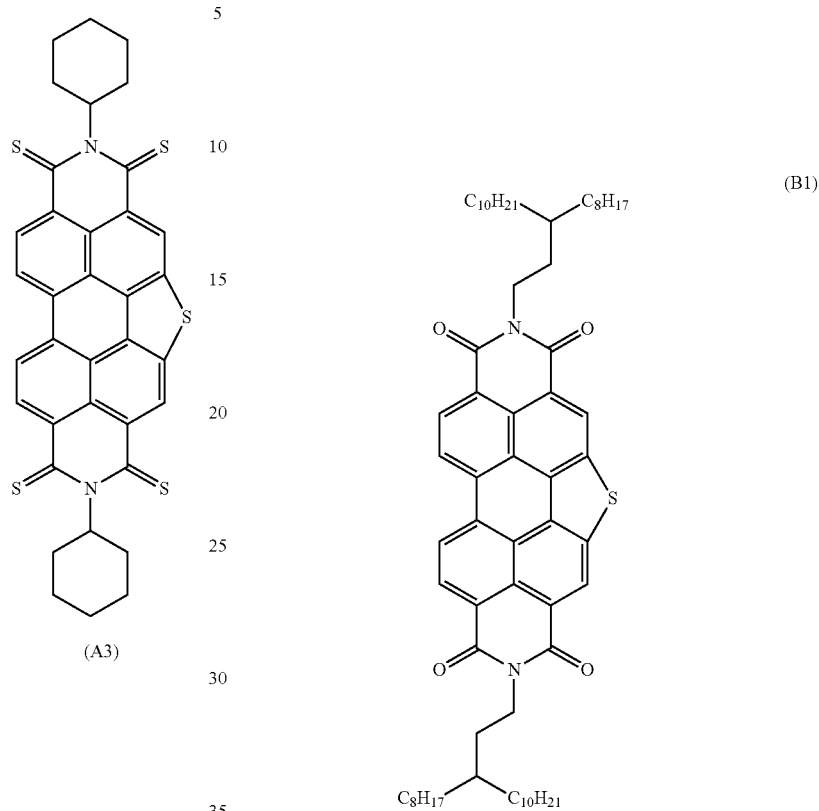

(A3)

First, a starting material (Formula (B3)) in Scheme (S2) was synthesized with reference to European Journal Of Organic Chemistry 2000. 2, 365 to 380.

Subsequently, the starting material (100 mg, 0.171 mmol), a Lawesson's reagent (291 mg, 0.718 mmol), and 3.4 mL of 1-methylnaphthalene were added, and stirring was performed at 180° C. for one hour. The reaction liquid was cooled down to room temperature and was purified by column chromatography (toluene:hexane=1:2) so as to obtain Example Compound 3 (5 mg, 4.5%, see Formula (A3)) as a blue solid. The structure of Example Compound 3 obtained was identified by $^1$H NMR.

Example Compound 3 $^1$H NMR (CDCl$_3$, 400 MHz) δ: 0.88-2.04 (16H, m), 2.70 (4H, br), 6.12 (2H, br), 8.61 (21-1, br), 9.13 (4H, br).

Comparative Compounds 1 and 2

Comparative Compound 1 (Formula (B1)) was a starting material of Example Compounds 1 and 2. Comparative Compound 2 (Formula (B2)) was synthesized with reference to Journal of Physical Chemistry C. 2014. 118, 9996 to 10004. Comparative Compound 3 (Formula (B3)) was a starting material of Example Compound 3. Comparative Compound 4 (Formula (B4)) and Comparative Compound 5 (Formula (B5)) were synthesized with reference to Chemica l Communications, 2006, 44, 4587 to 4589 and the synthesis method of Example Compound 1.

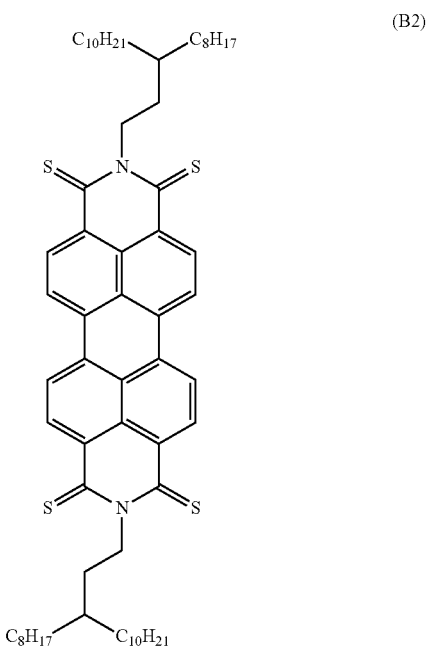

(B3)

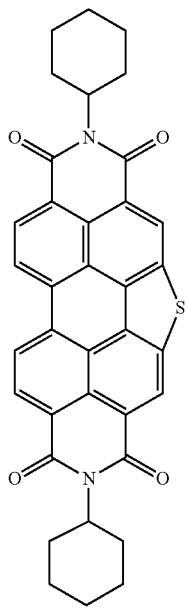

(B4)

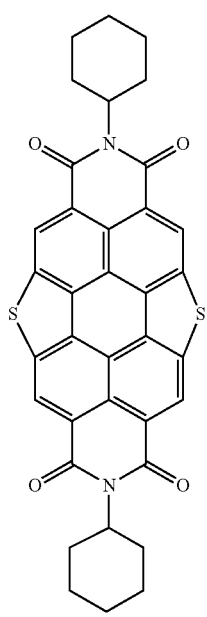

(B5)

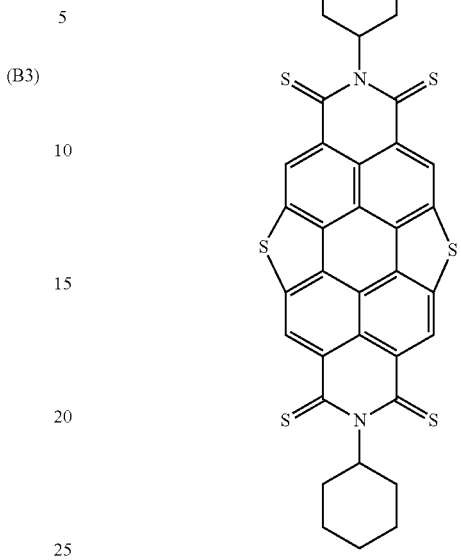

<Evaluation of Solubility to Organic Solvent>

2 mg of each example compound and comparative compound obtained above were weighed, and the saturated solubility (mass %) at room temperature (25° C.) was calculated from the volume and the specific gravity of toluene, chloroform, tetrahydrofuran, and N,N-dimethylformamide. Those having 2 mass % or greater were as set as "A", those having 1 mass % or greater and less than 2 mass % were set as "B", those having 0.1 mass % or greater and less than 1 mass % were set as "C", and those having less than 0.1 mass % were set as "D". Saturated solubility (hereinafter also referred to as solubility) of each compound in toluene, chloroform, tetrahydrofuran, and N,N-dimethylformamide was presented as Solubility (1) to (4), in the evaluation results of a first table.

<Manufacturing of Organic Thin Film Transistor and Evaluation of Carrier Mobility>

It was checked that the organic thin film transistor materials (example compounds and comparative compounds) used in the manufacturing of the organic thin film transistor had purity (absorption intensity area ratio at 254 nm) by high performance liquid chromatography of 99.0% or greater.

(Forming of Organic Semiconductor Film)

For any one of the respective example compounds and comparative compounds, a solution containing 0.05% by mass of butoxybenzene as a solvent was prepared and heated to 100° C., so as to obtain the organic thin film transistor compositions of examples and comparative examples.

Figure 3:
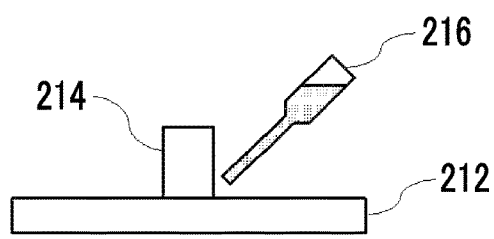
FIG. 3 is a schematic view illustrating a method of manufacturing an organic semiconductor film of examples and comparative examples.
Figure 4A:
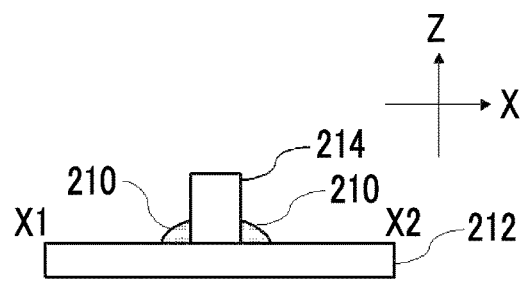
FIG. 4A is a schematic view illustrating the method of manufacturing the organic semiconductor film of examples and comparative examples.
Figure 4B:
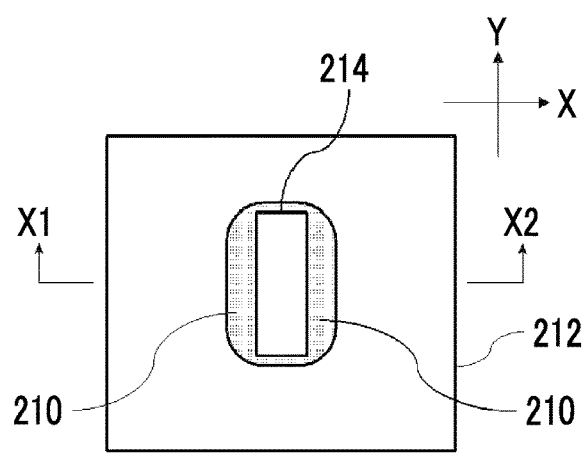
FIG. 4B is a schematic view illustrating the method of manufacturing the organic semiconductor film of examples and comparative examples.
Figure 5:
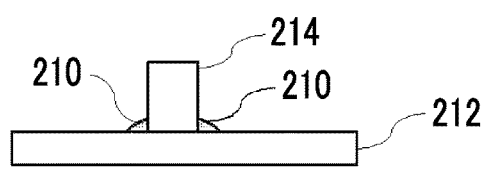
FIG. 5 is a schematic view illustrating the method of manufacturing the organic semiconductor film of examples and comparative examples.

In the examples and the comparative examples, organic semiconductor thin films were formed by the method described in FIGS. 3, 4A, 4B, and 5 (that is, FIGS. 3 to 5). FIGS. 3 to 5 are schematic views illustrating the method of manufacturing organic semiconductor films of the examples and the comparative examples. Details of the method of forming the organic semiconductor film are described below.

A 10 mm×10 mm substrate obtained by forming a 200 nm thermal oxide film of SiO$_2$ on the surface of the n-type silicon substrate (thickness of 0.4 mm) was used as a substrate 212. The surface of the thermal oxide film of the substrate 212 was subjected to an ultraviolet (UV)-ozone washing and a β-phenytiltrimethoxysilane treatment.

The substrate 212 and the member 214 were put in a manner of being in contact with each other at the center of the substrate 212 on the β-phenytiltrimethoxysilane treated side of the substrate 212, as illustrated in FIG. 3. The member 214 was made of glass and had a length of 7 mm, a width of 2 mm, and a height of 3 mm. The lateral direction (X-axis direction) in FIG. 3 was the lateral direction of the member 214, the vertical direction (Z-axis direction) in FIG. 3 was the height direction of the member 214, and the vertical direction (Y-axis direction) in FIG. 4B is a machine direction of the member 214.

The substrate 212 was heated to 95° C., and one drop (about 0.05 mL) of the organic thin film transistor composition (an organic thin film transistor composition 210 of FIGS. 3 to 5) prepared by the above method was suspended to the side portion of a member 214 by using a pipet 216 so as to come into contact with the both side of the substrate 212 and a member 214 as illustrated in FIG. 3, such that the organic thin film transistor composition 210 was added dropwise to a portion on the surface of the substrate 212 as illustrated in FIGS. 4A and 4B. A concave meniscus was formed on the interface to the member 214.

As illustrated in FIG. 5, the organic thin film transistor composition added dropwise was naturally dried in a state in which the substrate 212 and the member 214 are in contact with each other is maintained and in a state in which a positional relation between the substrate 212 and the member 214 is stopped. Thereafter, the organic thin film transistor composition was dried under reduced pressure at 90° C. for eight hours under a pressure of $10^{-3}$ MPa such that crystals of each of the above-mentioned example compounds and comparative compounds were precipitated, and thus an organic semiconductor film was formed. The precipitation of the crystals was checked by observation with a polarizing microscope. The film thickness of the obtained organic semiconductor film was 50 nm.

A mask was attached to the obtained organic semiconductor film, and a gold electrode of 40 nm was vapor-deposited, so as to obtain organic thin film transistors of examples and comparative examples for measuring carrier mobility.

(Evaluation of Carrier Mobility)

A voltage of −80 V was applied between a source electrode and a drain electrode of each organic thin film transistor (FET element), a gate voltage was changed to a range of 20 V to −100 V, an equation $I_d = (w/2L)\mu C_i (V_g - V_{th})^2$ (in the equation, L represents a gate length, w represents a gate width, $C_i$ represents a capacitance per unit area of the insulating layer, $V_g$ represents a gate voltage, and $V_{th}$ represents a threshold voltage) indicating a drain current $I_d$ was used, so as to calculate carrier mobility μ. Those having carrier mobility of $10^{-2}$ cm$^2$/Vs or greater were evaluated as "A", those having carrier mobility of $10^{-4}$ cm$^2$ or greater and less than $10^{-2}$ cm$^2$/Vs were evaluated as "B", and those having carrier mobility of less than $10^{-4}$ cm$^2$/Vs were evaluated as "C". The evaluation results are provided in a first table.

TABLE 13

| First table | Types of organic semiconductor material | Evaluation result ||||| 
| | | Solubility to organic solvent |||| Carrier mobility |
| | | Solubility (1) | Solubility (2) | Solubility (3) | Solubility (4) | |
|---|---|---|---|---|---|---|
| Example 1 | Example Compound 1 (Formula (A1)) | B | A | B | B | A |
| Example 2 | Example Compound 2 (Formula (A2)) | A | A | A | B | A |
| Example 3 | Example Compound 3 (Formula (A3)) | B | B | B | B | A |
| Comparative Example 1 | Comparative Compound 1 (Formula (B1)) | B | A | A | B | C |
| Comparative Example 2 | Comparative Compound 2 (Formula (B2)) | C | C | B | C | B |
| Comparative Example 3 | Comparative Compound 3 (Formula (B3)) | C | C | C | C | C |
| Comparative Example 4 | Comparative Compound 4 (Formula (B4)) | D | D | D | D | C |
| Comparative Example 5 | Comparative Compound 5 (Formula (B5)) | D | D | D | D | B |

From the evaluation results of the first table, it was understood that the compounds (Example Compound 1 to 3) represented by Formula (1) had excellent solubility to the organic solvent, and the organic thin film transistors of Examples 1 to 3 using the example compounds had excellent carrier mobility.

According to the comparison between Examples 1 and 2, it was found that, in a case where compounds formed of different atoms were used in at least two of $X_1$, $X_2$, $X_3$, and $X_4$ in Formula (1) (Example Compound 2 of Example 2), solubility to the organic solvent became excellent.

According to the comparison between Examples 1 and 3, it was found that, in a case where $R_1$ and $R_2$ in Formula (1) each were a branched alkyl group (Example Compound 1 of Example 1), solubility to the organic solvent became excellent.

Meanwhile, Comparative Compound 1 had an asymmetric structure in which a ring was added to a perylene diimide skeleton, but an oxygen atom in a carbodiimide structure was not substituted with a sulfur atom or selenium atom. It was found that, an organic thin film transistor of Comparative Example 1 manufactured by using Comparative Compound 1 had deteriorated carrier mobility.

Comparative Compound 2 had a symmetric structure in which an oxygen atom in a carbodiimide structure was substituted with a sulfur atom, but no ring was attached to a perylene diimide skeleton. Comparative Compound 2 had insufficient solubility depending on types of organic solvents and the organic thin film transistor of Comparative Example 2 manufactured by using this had insufficient carrier mobility.

Meanwhile, Comparative Compound 3 had an asymmetric structure in which a ring was added to a perylene diimide skeleton, but an oxygen atom in a carbodiimide structure was not substituted with a sulfur atom or a selenium atom. Comparative Compound 3 had insufficient solubility to an organic solvent, and the organic thin film transistor of Comparative Example 3 manufactured by using this had insufficient carrier mobility.

Comparative Compound 4 had a symmetric structure in which an oxygen atom in a carbodiimide structure was not substituted with a sulfur atom or a selenium atom and a ring was symmetrically attached to a perylene diimide skeleton. Comparative Compound 4 had insufficient solubility to an organic solvent and the organic thin film transistor of Comparative Example 4 manufactured by using this had deteriorated carrier mobility.

Comparative Compound 5 had a symmetric structure in which an oxygen atom in a carbodiimide structure was substituted with a sulfur atom, and a ring was symmetrically attached to a perylene diimide skeleton. Comparative Compound 5 had insufficient solubility to an organic solvent and the organic thin film transistor of Comparative Example 5 manufactured by using this had insufficient carrier mobility.

EXPLANATION OF REFERENCES

10: substrate
20: gate electrode
30: gate insulating film
40: source electrode
42: drain electrode
50: organic semiconductor film (organic semiconductor layer)
60: sealing layer
100, 200: organic thin film transistor
210: organic thin film transistor composition
212: substrate
214: member
216: pipet

What is claimed is:

1. An organic thin film transistor comprising: an organic semiconductor film containing a compound represented by Formula (1),

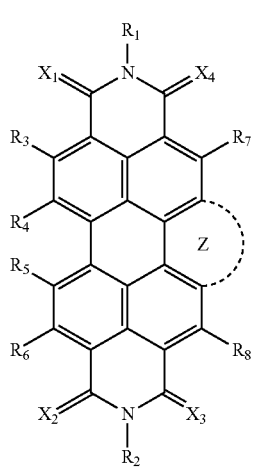

(1)

in Formula (1), $R_1$ and $R_2$ each independently represent a hydrogen atom, an alkyl group, an alkenyl group, an alkoxy group, an alkynyl group, a halogenated alkyl group, an aryl group, and a heteroaryl group, $R_3$, $R_4$, $R_5$, $R_6$, $R_7$, and $R_8$ each independently represent a hydrogen atom, an alkyl group, an alkenyl group, an alkoxy group, an alkynyl group, a halogenated alkyl group, an aryl group, a heteroaryl group, a halogen atom, a nitro group, and a cyano group, $R_3$ and $R_4$ may form a ring, and $R_5$ and $R_6$ may form a ring, Z is a 5-membered ring containing a sulfur atom or a selenium atom, and $X_1$, $X_2$, $X_3$, and $X_4$ each independently represent an oxygen atom, a sulfur atom, or a selenium atom, and at least one of $X_1$ to $X_4$ is a sulfur atom or a selenium atom.

2. The organic thin film transistor according to claim 1, wherein, in Formula (1), the number of carbon atoms included in $R_1$ and the number of carbon atoms included in $R_2$ are each independently 30 or less.

3. The organic thin film transistor according to claim 1, wherein, in Formula (1), $R_1$ and $R_2$ each independently represent an alkyl group.

4. The organic thin film transistor according to claim 1, wherein, in Formula (1), $R_1$ and $R_2$ are the same groups, $R_3$ and $R_6$ are the same groups, and $R_4$ and $R_5$ are the same groups.

5. The organic thin film transistor according to claim 1, wherein, the compound represented by Formula (1) is a compound represented by Formula (2),

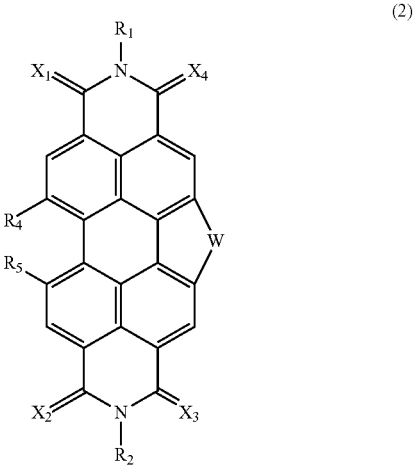

(2)

in Formula (2), $R_1$ and $R_2$ are the same groups, and are alkyl groups having 30 or less carbon atoms, $R_4$ and $R_5$ each have the same meaning as $R_4$ and $R_5$ in Formula (1), and $R_4$ and $R_5$ are the same groups, W represents a sulfur atom or a selenium atom, and $X_1$, $X_2$, $X_3$, and $X_4$ each have the same meaning as $X_1$, $X_2$, $X_3$, and $X_4$ in Formula (1).

6. The organic thin film transistor according to claim 1, wherein, in Formula (1), at least two of $X_1$, $X_2$, $X_3$, and $X_4$ are formed of different atoms.

7. A compound represented by Formula (1),

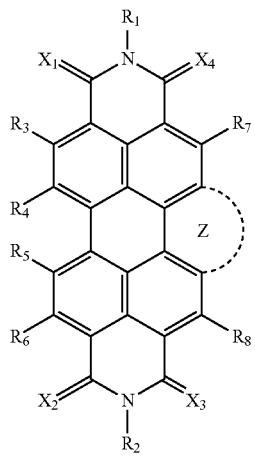

in Formula (1), $R_1$ and $R_2$ each independently represent a hydrogen atom, an alkyl group, an alkenyl group, an alkoxy group, an alkynyl group, a halogenated alkyl group, an aryl group, and a heteroaryl group, $R_3$, $R_4$, $R_5$, $R_6$, $R_7$, and $R_8$ each independently represent a hydrogen atom, an alkyl group, an alkenyl group, an alkoxy group, an alkynyl group, a halogenated alkyl group, an aryl group, a heteroaryl group, a halogen atom, a nitro group, and a cyano group, $R_3$ and $R_4$ may form a ring, and $R_5$ and $R_6$ may form a ring, Z is a 5-membered ring containing a sulfur atom or a selenium atom, and $X_1$, $X_2$, $X_3$, and $X_4$ each independently represent an oxygen atom, a sulfur atom, or a selenium atom, and at least one of $X_1$ to $X_4$ is a sulfur atom or a selenium atom.

8. The compound according to claim 7, wherein, in Formula (1), the number of carbon atoms included in $R_1$ and the number of carbon atoms included in $R_2$ are each independently 30 or less.

9. The compound according to claim 7, wherein, in Formula (1), $R_1$ and $R_2$ each independently represent an alkyl group.

10. The compound according to claim 7, wherein, in Formula (1), $R_1$ and $R_2$ are the same groups, $R_3$ and $R_6$ are the same groups, and $R_4$ and $R_5$ are the same groups.

11. The compound according to claim 7, wherein, the compound represented by Formula (1) is a compound represented by Formula (2),

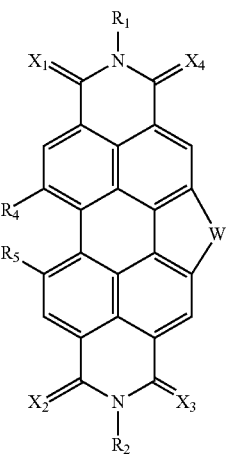

in Formula (2), $R_1$ and $R_2$ are the same groups, and are alkyl groups having 30 or less carbon atoms, $R_4$ and $R_5$ each have the same meaning as $R_4$ and $R_5$ in Formula (1), and $R_4$ and $R_5$ are the same groups, W represents a sulfur atom or a selenium atom, and $X_1$, $X_2$, $X_3$, and $X_4$ each have the same meaning as $X_1$, $X_2$, $X_3$, and $X_4$ in Formula (1).

12. The compound according to claim 7, wherein, in Formula (1), at least two of $X_1$, $X_2$, $X_3$, and $X_4$ are formed of different atoms.

13. An organic thin film transistor material containing the compound according to claim 7.

14. An organic thin film transistor composition containing the compound according to claim 7.

15. An organic semiconductor film containing the compound according to claim 7.

16. A method of manufacturing an organic thin film transistor, comprising: a step of coating a substrate with the organic thin film transistor composition according to claim 14 and drying the composition to form an organic semiconductor film.

17. The organic thin film transistor according to claim 2, wherein, in Formula (1), $R_1$ and $R_2$ each independently represent an alkyl group.

18. The organic thin film transistor according to claim 2, wherein, in Formula (1), $R_1$ and $R_2$ are the same groups, $R_3$ and $R_6$ are the same groups, and $R_4$ and $R_5$ are the same groups.

* * * * *